(12) United States Patent
Guarda et al.

(10) Patent No.: US 9,334,213 B2
(45) Date of Patent: May 10, 2016

(54) PROCESS FOR THE ALKOXYLATION OF (PER) FLUOROPOLYETHER ALCOHOLS

(71) Applicant: SOLVAY SPECIALTY POLYMERS ITALY S.P.A., Bollate (IT)

(72) Inventors: Pier Antonio Guarda, Arese (IT); Gianfranco Spataro, Lissone (IT)

(73) Assignee: SOLVAY SPECIALTY POLYMERS ITALY S.P.A., Bollate (Milano) (IT)

( * ) Notice: Subject to any disclaimer, the term of this patent is extended or adjusted under 35 U.S.C. 154(b) by 0 days.

(21) Appl. No.: 14/651,542

(22) PCT Filed: Dec. 4, 2013

(86) PCT No.: PCT/EP2013/075476
§ 371 (c)(1),
(2) Date: Jun. 11, 2015

(87) PCT Pub. No.: WO2014/090649
PCT Pub. Date: Jun. 19, 2014

(65) Prior Publication Data
US 2015/0329453 A1    Nov. 19, 2015

(30) Foreign Application Priority Data
Dec. 11, 2012 (EP) ..................................... 12196554

(51) Int. Cl.
| | | |
|---|---|---|
| C07C 41/08 | (2006.01) |
| C07C 41/18 | (2006.01) |
| C08G 65/26 | (2006.01) |
| C08G 65/00 | (2006.01) |
| C08G 65/331 | (2006.01) |
| C08G 65/328 | (2006.01) |

(52) U.S. Cl.
CPC .............. *C07C 41/18* (2013.01); *C08G 65/007* (2013.01); *C08G 65/2609* (2013.01); *C08G 65/2654* (2013.01); *C08G 65/2687* (2013.01); *C08G 65/2696* (2013.01); *C08G 65/328* (2013.01); *C08G 65/331* (2013.01); *C08G 2650/48* (2013.01)

(58) Field of Classification Search
None
See application file for complete search history.

(56) References Cited

U.S. PATENT DOCUMENTS

| | | |
|---|---|---|
| 2,723,999 A | 11/1955 | Cowen et al. |
| 3,442,942 A | 5/1969 | Sianesi et al. |
| 3,665,041 A | 5/1972 | Sianesi et al. |
| 3,715,378 A | 2/1973 | Sianesi et al. |
| 3,766,251 A | 10/1973 | Caporiccio et al. |
| 3,847,978 A | 11/1974 | Sianesi et al. |
| 4,490,561 A | 12/1984 | Yang et al. |
| 4,647,413 A | 3/1987 | Savu |
| 5,258,110 A | 11/1993 | Sianesi et al. |
| 5,777,291 A | 7/1998 | Marchionni et al. |
| 6,509,509 B2 | 1/2003 | Tonelli et al. |
| 6,573,411 B2 | 6/2003 | Russo et al. |
| 7,132,574 B2 | 11/2006 | Picozzi et al. |
| 8,039,677 B2 | 10/2011 | Peng et al. |
| 2010/0280280 A1 | 11/2010 | Peng et al. |

FOREIGN PATENT DOCUMENTS

| | | |
|---|---|---|
| EP | 151877 A2 | 8/1985 |
| SU | 550377 A1 | 3/1977 |
| SU | 570590 A1 | 8/1977 |
| WO | 9535272 A1 | 12/1995 |
| WO | 9628407 A2 | 9/1996 |
| WO | 2008122639 A1 | 10/2008 |
| WO | 2009073641 A1 | 6/2009 |
| WO | 2010127221 A1 | 11/2010 |
| WO | 2010127230 A2 | 11/2010 |
| WO | 2012139070 A1 | 10/2012 |

*Primary Examiner* — Rosalynd Keys

(57) ABSTRACT

A convenient process for the manufacture of alkoxylated derivatives of PFPE alcohols is herein provided. The process envisages the use of a boron-based catalyst and an iodine source and is characterized in that a PFPE alkoxide is prepared separately, contacted with a boric acid triester of the same PFPE alcohol and finally submitted to alkoxylation in the presence of an iodine source. The process allows achieving an alkoxylation degree of at least 2 with high yields and under conditions that are convenient on an industrial scale.

18 Claims, No Drawings

PROCESS FOR THE ALKOXYLATION OF (PER) FLUOROPOLYETHER ALCOHOLS

This application is a U.S. national stage entry under 35 U.S.C. X371 of International Application No. PCT/EP2013/075476 filed Dec. 4, 2013, which claims priority to European application No. 12196554.5, filed on Dec. 11, 2012. The entire contents of these applications are explicitly incorporated herein by this reference.

TECHNICAL FIELD

The present invention relates to an alkoxylation process, in particular to an alkoxylation process for the manufacture of alkoxylated derivatives of (per)fluoropolyethers having a defined alkoxylation degree.

BACKGROUND ART

Alkoxylated derivatives of fluorinated alcohols having a low alkoxylation degree, typically ranging from 2 to 10, and in particular ethoxylated derivatives of (per)fluoropolyether (PFPE) alcohols, are useful building blocks for the synthesis of further functional derivatives and mixed copolymers. Indeed, the presence of a short polyethyleneoxy chain at the polymer ends improves compatibility with hydrogenated reagents, which is particularly desirable in the synthesis of copolymers with hydrogenated blocks. Compatibility with hydrogenated compounds may also be an advantage in the manufacture of compositions wherein a PFPE alcohols is to be mixed with hydrogenated ingredients.

However, while ethoxylated derivatives of PFPEs alcohols having an ethoxylation degree from 1 to about 2 can be synthesised by reaction of a PFPE alcohol with ethylene oxide in the presence of a catalytic amount of the corresponding PFPE alkoxide, ethoxylated derivatives having an ethoxylation degree equal to or higher than 2 cannot.

In order to overcome this drawback, attempts to develop alternative methods have been made.

A number of prior art documents disclose the use of boron-based catalysts in the manufacture of ethoxylated derivatives of fluorinated alcohols.

For example, inventor's certificate SU 570590, granted to Fedorov V. A. et al. on Aug. 30, 1977, relates to the synthesis of non-ionic surface agents by reaction of fluorinated alcohols of formula $H(CF_2)_nCH_2OH$, in which n ranges from 4 to 12, with an alkylene oxide in the presence of boron trifluoride etherate as catalyst.

U.S. Pat. No. 4,490,561 (CONOCO INC [US]) 25 Dec. 1984 discloses a method for the alkoxylation of fluorinated alcohols which comprises contacting a fluorinated alcohol with an alkoxylating agent in the presence of a catalyst selected from a specific group (reference is made in particular to claim 1). The group includes, inter alia, a $BF_3/M(R)_q$ catalyst, wherein M is a metal selected from gallium, indium, thallium, zirconium, hafnium, aluminium and titanium, q is equal to the valence of M and R is hydrogen, fluorine, an alkyl group, or an alkoxy group. In particular, fluorinated alcohols that can be submitted to this ethoxylation methods comply with the following formulae (reference is made in particular to col. 2, lines 41-63):

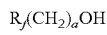  (5)

  (6)

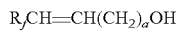  (7)

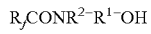  (8)

wherein $R_f$ represents straight or branched perfluoroalkyl groups, $R^1$ is an alkylene group containing from 2 to 30 carbon atoms and $R^2$ is, independently, hydrogen, halogen, or an alkyl group containing from 1 to 30 carbon atoms.

WO 95/35272 A (DU PONT [US]) 28 Dec. 1995 discloses a process for the preparation of mixtures of fluoroalkoxylates of formula:

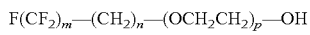

wherein:
$F(CF_2)_m$ is a linear perfluoroalkyl group;
m is an integer in the range between 2 and about 20;
n is an integer in the range between 1 and 3; and
p is an integer in the range between 1 and about 40;
said process comprising reacting a perfluoroalkanol of formula:

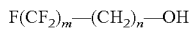

wherein m and n are as defined above
with ethylene oxide in the presence of a catalyst consisting essentially of a mixture of an alkali metal borohydride and at least one source of iodine selected from elemental iodine, alkali metal iodides, and alkaline earth metal iodides.

WO 96/28407 (DU PONT [US]) 19 Sep. 1996 (corresponding to U.S. Pat. No. 5,608,116), relates to a process for preparing fluoroalkyl ethoxylated alcohols by reaction of a fluorinated alcohol with an alkylene epoxide having from 2 to 10 carbon atoms, in particular, ethylene oxide, in the presence of an alkali metal borohydride and of at least an iodine source. In particular, the fluorinated alcohol complies with formula:

in which $R_f$ is a linear or branched perfluoroalkyl group having from 4 to 20 carbon atoms, or a mixture of these groups; and
Q is $—(CH_2)_n—$, $—SO_2NR^1R^2—$ or $—C(O)—NR^3R^4—$
wherein each of $R^1$ and $R^4$ is independently hydrogen or an alkyl group containing from 1-6 carbon atoms; each of $R^2$ and $R^3$ is independently a divalent linear or branched alkylene group containing from 1-6 carbon atoms; and n is an integer of from 1 to 6.

U.S. Pat. No. 8,039,677 B (DU PONT [US]) 4 Nov. 2010 relates to fluoroalkoxylates to be used for altering the surface behaviour of liquids. In particular, this document discloses fluorinated alkylalkoxylates containing a perfluoroalkyl group having less than 8 carbon atoms, which are prepared by means of a process comprising reacting an alcohol of formula:

  (4)

in which:
$R_f$ is a linear or branched perfluoroalkyl group of 1 to 6 carbon atoms;
n is an integer from 1 to 4;
X is O; and
m is an integer from 1 to 6,
with one or more alkoxylating agents, such as alkylene epoxide, in the presence of a catalytic system comprising (1) at least one alkali metal borohydride and (2) at least one quaternary salt. Optionally, an iodine source can be present in the catalytic system. The results reported in the examples (reference is made in particular to tables 1 and 3) disclose in particular fluoroalkoxylates with an alkoxylation degree between 6 and 7.

WO 2010/127221 A (DU PONT [US]) 4 Nov. 2010 specifically discloses and claims a process as defined in U.S. Pat. No. 8,039,677 wherein the alkoxylating agent is an alkylene oxide having from 2 to 10 carbon atoms.

WO 2009/073641 (CHEMGUARD LTD) 6 Nov. 2009 relates to a method of forming an alkoxylated fluoroalcohol comprising combining:
a boron compound having or providing at least one boron-oxygen bond and an iodine source with
a fluoroalcohol and an alkylene oxide
in the presence of a base and
allowing the reactants to react to form an alkoxylated fluoroalcohol reaction product.

As fluoroalcohol subjected to the ethoxylation method, this document specifically mentions only a monofunctional per-fluorinated alkyl alcohol of formula:

$F(CF_2)_m$—OH or $F(CF_2)_m$—A—OH in which:
m usually ranges from 2 to 20, more preferably from 4 to 14, and
A can be a group of formula —$(CH_2)_n$—, —$SO_2NR^1R^2$ or a group of formula —$C(O)NR^3R^4$—, wherein n is from 1 to 6, $R^1$ and $R^4$ are each independently selected from hydrogen, halogen and a $C_1$-$C_{30}$ alkyl group and $R^2$ and $R^3$ are each independently selected from a $C_2$-$C_{30}$ alkylene group.

Boric acid or alkyl borates, potassium iodide, ethylene oxide and KOH are specifically mentioned respectively as boron compound, iodine source, alkylene oxide and base.

Alkoxylation of mono- and bi-functional PFPE alcohols is not mentioned or suggested in this document. Furthermore, this document teaches (reference is made to the paragraph bridging pages 9 and 10 and to examples 1 to 3) to carry out the alkoxylation reaction by first adding a base, namely NaOH, to the fluoroalcohol, followed by addition of the iodide source and of the boron compound; finally, the alkoxylating agent is added and the mixture is heated up to a temperature which might reach 200° C. in order to allow the ethoxylation reaction to proceed. In particular, it stems from examples 1 to 3 that the stoichiometric ratio between the base and boric acid or alkyl borate is lower than 1:1 and that the temperature raises at most to 155° C. However, attempts made by the applicant to carry out the ethoxylation of PFPE alcohols (in particular PFPE alcohols having —$CF_2$—$CH_2OH$ end groups), following this teaching did not provide the expected results, as shown in the following Experimental section in comparative example 4.

WO 2010/127230 A (DU PONT) 11 Nov. 2010 discloses a process for preparing alkoxylated alcohols alkoxylate of the formula $R^1O(QO)_mH$ wherein m is from 1 to 20, said process comprising contacting one or more alcohols of the formula $R^1OH$ with one or more 1,2-alkylene epoxides of the formula Q(O), wherein:
Q is a linear alkylene group of the formula $C_yH_{2y+1}$ where y is an integer of from 2 to 10, and
$R^1$ is a linear, branched, cyclic, or aromatic hydrocarbyl group, optionally substituted, having from 1 to 30 carbon atoms.

The process, aimed at avoiding the use of strong bases, envisages the use of a catalyst at a molar ratio of alcohol to catalyst of from about 200 to 15, wherein the catalyst is $MB(OR^1)_x(X)_{4-x}$ or $B(OR^1)_3/MX$, and wherein M is $Na^+$, $K^+$, $Li^+$, or $R^2R^3R^4R^5N^+$, $R^2R^3R^4R^5P^+$, and $R^2$, $R^3$, $R^4$, and $R^5$ independently are hydrocarbyl groups, X is Br, F or I and x is 1 to 3. The process is carried out at a temperature from about 60° C. to about 200° C. and at a pressure from ambient atmospheric pressure to about 1,035 KPa.

This document teaches that the process includes contacting the fluorinated alcohol with an alkylene oxide in the presence of the catalyst and it states that "the alcohol and catalyst can be added to the alkylene oxide either simultaneously or in any order" and that "the catalyst is either added to or generated in, the neat alcohol, which also serves as solvent for the reaction" (reference is made to page 5, lines 28-32).

This prior art document does not specifically disclose or suggests the alkoxylation of mono- or bifunctional PFPE alcohols. Attempts made by the applicant to carry out the ethoxylation of such alcohols (in particular PFPE alcohols having —$CF_2$—$CH_2OH$ end groups) following the teaching therein contained, in particular at examples 34 and 35, wherein no alkoxide of the fluorinated alcohol is used, in order to obtain ethoxylated derivatives with an ethoxylation degree of at least 2 did not provide the expected results, as shown in the following Experimental section in comparative example 5.

WO 2012/139070 (E.I. DU PONT DE NEMOURS AND COMPANY) is directed to fluoroalkoxylates having formula:

$R_f$—O—$(CF_2)_x(CH_2)_y$—O-$(QO)_z$—H     (1)

$R_f$ is a linear or branched perfluoroalkyl having 1 to 6 carbon atoms optionally interrupted by one to three ether oxygen atoms;
x is an integer of 1 to 6;
y is an integer of 1 to 6;
Q is a linear 1,2-alkylene group of the formula $C_mH_{2m}$ where m is an integer of 2 to 10; and
z is an integer of 1 to 30.

This document teaches to prepare the compounds of formula (1) in the presence of a catalyst system comprising (a) at least one boron-containing compound and (b) a source of iodine or bromine. In greater detail, in Examples 1 it is taught to prepare a mixture of perfluoropropylvinylether alcohol (PPVE alcohol), a boron-containing compound (sodium borohydride) and an iodine compound (sodium iodide); the mixture is then treated with ethylene oxide to obtain ethoxylates with varying linkages. In Example 2 it is taught to charge a reactor with $HOCH_2CH_2CF_2CF_2OCF_2CF_2CF_3$, 6% mol of the corresponding triboric ester and 6% mol tetrabutylammonium iodide and then treating with ethylene oxide to obtain a compound with an ethoxylation degree of 8. No specific mention is made of the alkoxylation of fluorinated alcohols ending with a —$CF_2$—$CH_2OH$ moiety and of the use of an alkoxide of the fluorinated alcohol in the process.

The need was thus felt to provide a convenient industrial process for the manufacture of alkoxy derivatives of PFPE alcohols having an alkoxylation degree of at least 2.

SUMMARY OF INVENTION

It has now been found that the above need is fulfilled by a process wherein a boron-based catalytic species is prepared by first providing a mixture of a PFPE alcohol containing a catalytic amount of the corresponding alkoxide and then bringing into contact such mixture with a catalytic amount of a boric acid triester of the same PFPE alcohol.

In greater detail, the process of the invention comprises the following steps:
1) separately providing a mixture [M1], comprising a PFPE alcohol and a catalytic amount of the corresponding alkoxide (herein after "PFPE-alk");
2) bringing into contact mixture [M1] with a boric acid triester of the same PFPE alcohol (herein after "PFPE-tri-Bor") in such an amount that the molar ratio PFPE-alk:PFPE-triBor is at least 1, to obtain a mixture [M2];

3) contacting mixture [M2] with a catalytic amount of an iodine source to obtain a mixture [M3];

4) treating mixture [M3] with an alkoxylating agent to provide a mixture [M4] containing an alkoxylated derivative of the PFPE alcohol.

It has indeed been observed that by separately preparing the PFPE-alk from the PFPE-triBor it is possible to obtain ethoxylated derivatives of PFPE alcohols having an ethoxylation degree of at least 2, preferably from 3 to 10 (in the following description it is intended that range extremes are included), more preferably from 4 to 6 in good yields and under conditions (reaction time, temperature and pressure) that are particularly suitable on an industrial scale, as it will be clearer from the following description.

For the purposes of the present description, the term "(per)fluoropolyether (PFPE) alcohol" is meant to denote a polymer comprising a partially or fully fluorinated, straight or branched, polyoxyalkylene chain (chain $R_f$) having at least two chain ends, wherein one or both chain end(s) bear(s) at least one hydroxyl group. According to a first embodiment, the PFPE alcohol comprises an $R_f$ chain having two chain ends, wherein one chain end bears one hydroxyl group (herein after "monofunctional PFPE alcohol); according to a second embodiment, the PFPE alcohol comprises an $R_f$ chain having two chain ends, wherein each chain end bears one hydroxyl group (herein after "bifunctional PFPE alcohol or PFPE-diol").

PFPE alcohols which can be submitted to the alkoxylation process of the invention can be represented in particular by formula (I) here below:

$$A-O-R_f-(CF_2)_x-CFZ-CH_2OH \quad (I)$$

wherein:

$R_f$ is a (per)fluoropolyoxyalkylene chain having an average number molecular weight $M_n$ ranging from 100 to 8,000, preferably from 300 to 6,000, more preferably from 800 to 3,000, and comprising repeating units, which may be equal to or different from one another, selected from the following groups: (CFYO), wherein Y is F or $CF_3$; ($CF_2CF_2O$); ($C_3F_6O$), including ($CF_2CF_2CF_2O$), ($CF_2CF(CF_3)O$) and ($CF(CF_3)CF_2O$); and ($CF_2CF_2CF_2CF_2O$)

Z is fluorine or $CF_3$;

x is 0 or 1, with the proviso that, when, x is 1, Z is F;

A is $(CF_2)_x$—CFZ—$CH_2OH$ or is selected from straight or branched $C_1$-$C_4$ perfluoroalkyl groups wherein one fluorine atom can be substituted by one chlorine atom or one hydrogen atom; when chlorine is present in a non-functional group A or B, it is in a molar amount lower than 2% with respect to the overall amount of end groups.

Preferred examples of compounds of formula (I) are those wherein chain $R_f$ is selected from the following classes:

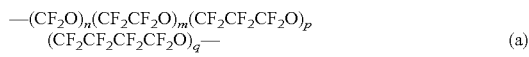
(a)

wherein m, n, p, q are 0 or integers selected in such a way as chain $R_f$ meets the above number average molecular weight requirement; when m is other than 0, the m/n ratio is preferably between 0.1 and 20; when (m+n) is other than 0, (p+q)/(m+n) is preferably between 0 and 0.2, extremes included;

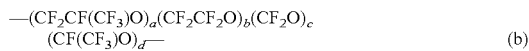
(b)

wherein a, b, c, d are 0 or integers selected in such a way as chain $R_f$ meets the above number average molecular weight requirement; when b is other than 0, a/b is preferably between 0.1 and 10; when (a+b) is different from 0 (c+d)/(a+b) preferably is between 0.01 and 0.5, more preferably between 0.01 and 0.2;

(c)

wherein e, f, g are 0 or integers selected in such a way as chain $R_f$ meets the above number average molecular weight requirement; when e is other than 0, (f+g)/e is preferably between 0.01 and 0.5, more preferably between 0.01 and 0.2.

Preferred PFPE alcohols of formula (I) can be manufactured by chemical reduction of corresponding PFPE carboxylic acids or esters according to several methods known in the art, using reducing agents such as $NaBH_4$, or by catalytic hydrogenation, as disclosed, for example, in U.S. Pat. No. 6,509,509 (AUSIMONT SPA) 5 Jul. 2001, U.S. Pat. No. 6,573,411 (AUSIMONT SPA) 21 Nov. 2002, WO 2008/122639 (SOLVAY SOLEXIS SPA) 16 Oct. 2008. Precursors of PFPE carboxylic acids or of PFPE esters can be manufactured according to different methods, e.g. by oxypolymerization of fluoroolefins or by ring opening polymerization of HFPO (hexafluoropropylene oxide), as taught in U.S. Pat. No. 3,847,978 (MONTEDISON SPA) 12 Nov. 1974, U.S. Pat. No. 3,766,251 (MONTEDISON SPA) 16 Oct. 1973 U.S. Pat. No. 3,715,378 (MONTEDISON SPA) 6 Feb. 1973 U.S. Pat. No. 3,665,041 (MONTEDISON SPA) 23 May 1972, U.S. Pat. No. 4,647,413 (MINNESOTA MINING & MFG) 3 Mar. 1987, EP 151877 A (MINNESOTA MINING & MFG) 21 Aug. 1985 U.S. Pat. No. 3,442,942 (MONTEDISON SPA) 6 May 1969, U.S. Pat. No. 577,291 (AUSIMONT SPA) 7 Jul. 1998, U.S. Pat. No. 5,258,110 (AUSIMONT SRL) 2 Nov. 1993 or U.S. Pat. No. 7,132,574 B (SOLVAY SOLEXIS SPA) 7 Nov. 2006.

According to a preferred embodiment of the invention, the PFPE alcohol of formula (I) is a PFPE diol, i.e. an alcohol of formula (I) wherein A is —$(CF_2)_x$—CFZ—$CH_2OH$, wherein x and Z are as defined above.

According to a further preferred embodiment of the invention, in the PFPE alcohol (I) chain $R_f$ is a chain belonging to class (a); more preferably, the PFPE alcohol is a PFPE diol, i.e. an alcohol of formula (I) wherein A is (CF 2)$_x$—CFZ—$CH_2OH$, wherein x and Z are as defined above, more preferably wherein A is —$CF_2CH_2OH$.

In step 1) of the process of the present invention, mixture [M1] is typically prepared by adding a base to the PFPE alcohol of formula (I) and by allowing the base to react with the PFPE alcohol and form a catalytic amount of the corresponding PFPE-alk dissolved in the PFPE alcohol. The base can be selected from metal hydrides or hydroxides like NaOH, KOH, Ca(OH)$_2$ and Mg(OH)$_2$; according to a preferred embodiment of the invention, the base is KOH. Typically, the base is used in such an amount to obtain from 1 to 15%, preferably from 2 to 12% of PFPE-alk with respect to the PFPE alcohol. Accordingly, for the purposes of the present invention, the expression "catalytic amount of PFPE-alk" is intended to mean a molar amount ranging from 1 to 15% mol, more preferably from 2 to 12% mol with respect to the PFPE alcohol. When a metal hydroxide is used as base, the reaction is typically promoted by heating and the proceeding of the reaction is checked by monitoring the amount of water evaporated off the reaction mixture. When a metal hydride is used as base the proceeding of the reaction is checked by monitoring the amount of hydrogen evaporated off the reaction mixture.

Step 2) of the process of the invention can be performed in two different ways. In a first preferred embodiment, illustrated in detail in example 1 below, a mixture containing a PFPE-triBor and the PFPE alcohol (herein after referred to as mixture [M$_{est}$]) is prepared and then brought into contact with mixture [M1]. Typically, [M$_{est}$] is prepared by adding boric acid or a boric acid ester (including mono-, di- and tri-alkyl esters), and allowing the reagents to react until completion of the reaction, i.e. until obtainment of the PFPE-triBor in admixture with the PFPE alcohol. Typically, the esterification reaction is carried out under vacuum and with heating and the completion is checked by monitoring the amount of water (in case boric acid is used) or alcohol (in case an alkyl ester of boric acid is used) evaporated off the reaction mixture. In a second preferred embodiment, illustrated in example 2 below, the PFPE-triBor is prepared in situ, i.e. by adding to [M1] a boric acid trialkyl ester as defined above; also in this case the reaction is typically carried out under vacuum and with heating and the completion of the reaction is checked in the same way.

In the process of the invention, the molar ratio between the PFPE-alk and the PFPE-triBor is at least 1; according to a preferred embodiment, the PFPE-alk is used in excess with respect to PFPE-triBor, i.e. the molar ratio is higher than 1; still more preferably, the molar ratio is of at least 2. Indeed, it has been observed that when a molar ratio of at least 2 is used, the reaction proceeds faster and a higher conversion is achieved.

Step 3) of the process of the invention is typically carried out by adding a catalytic amount of an iodine source, to reaction mixture [M2]. The iodine source can be selected from one or more alkali- or alkaline-earth metal iodides, such as NaI, KI, CaI$_2$, ammonium iodides, such as NH$_4$I, elemental iodine and combinations thereof. According to a preferred embodiment, the iodine source is KI. A catalytic amount of iodine source is typically an equivalent amount ranging from 0.01 to 5% with respect to the fluoroalcohol.

Step 4) of the process of the invention is typically carried out by adding to mixture [M3] an alkoxylating agent in such a stoichiometric amount with respect to the fluoroalcohol as to obtain the desired alkoxylation degree. An alkoxylating agent to be used in the process of the invention typically complies with formula (II) below:

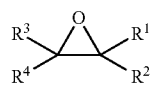
(II)

wherein R$^1$-R$^4$, equal to or different from one another, are selected from hydrogen, straight or branched C$_1$-C$_4$ alkyl.

Preferred examples of compounds of formula (II) are ethylene oxide and propylene oxide; according to a more preferred embodiment, the alkoxylating agent is ethylene oxide.

The alkoxylation reaction is typically carried out by adding to mixture [M3] one or more aliquots of the alkoxylation agent and by monitoring the consumption of the alkoxylation agent and the formation of the alkoxylated PFPE alcohol. When ethylene oxide is used as alkoxylating agent, the reaction is monitored by checking the ethylene oxide pressure in the reactor. The reaction is typically carried out under heating at a temperature usually ranging from 90° C. to 190° C. When ethylene oxide is used as alkoxylating agent, the reaction is carried out at temperatures usually ranging from 110° to 160° C.

Once the reaction is complete, the resulting ethoxylated PFPE alcohol can be isolated from mixture [M4] by conventional techniques, including extraction and distillation. Usually, mixture [M4] is cooled down to room temperature and then diluted with a fluorinated solvent, then treated with a water solution of an inorganic base, typically a carbonate, and the organic phase is separated and submitted to distillation. Examples of fluorinated solvents include, for example, Galden® PFPEs, hydrofluoroethers (HFEs) including Novec® HFEs, hydrofluorocarbons (HFCs), like Vertel® or Fluorinert®, and fluoroaromatic solvents like hexafluorobenzene and 1,3-hexafluoroxylene. Typically, the fluorinated solvent is 1,3-hexafluoroxylene.

The process of the invention allows obtaining in high yield (conversion degree higher than 95%) alkoxylated derivatives of PFPE alcohols under conditions that are convenient on an industrial scale and, in particular, it allows obtaining alkoxylated derivatives of PFPE alcohols having an ethoxylation degree of at least 2, typically from 3 to 10.

The invention will be illustrated in greater detail in the experimental section and non-limiting examples reported below.

Should the disclosure of any patents, patent applications, and publications which are incorporated herein by reference conflict with the description of the present application to the extent that it may render a term unclear, the present description shall take precedence.

EXPERIMENTAL SECTION

Materials and Methods

Fomblin® Z-DOL PFPE commercially available from Solvay Specialty Polymers was used.

The rest of reagents and solvents were purchased from Sigma-Aldrich and used as received.

$^1$H-NMR and $^{13}$H-NMR spectra were recorded on a Agilent System 500 operating at 499.86 MHz for $^1$H and 470.30 MHz for $^{19}$F.

Inductively Coupled Plasma (ICP) analyses were carried out with a Perkin Elmer ICP-OES spectrometer, model Optima 4300 DV.

Examples

Example 1

Sythesis of an Ethoxylated PFPE Diol with Average Ethoxylation Degree of 4.4

Preparation of Mixture [Mest] (Triester of Fomblin® Z-DOL PFPE with Boric Acid)

1.50 kg of a PFPE diol of formula:

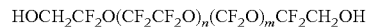

wherein m/n=1.2, the average molecular weight M$_n$ is 1,700 and the equivalent weight Ew is 865 (herein after Fomblin® Z-DOL PFPE) were charged in 2 L-reactor, equipped with a mechanical stirrer, a mechanical vacuum pump and a cold trap before the pump. One equivalent of boric acid (10.7 g, 173 mmoles) was added and the resulting mixture was stirred and heated at 80° C. with an oil bath, then vacuum was applied to the reactor, keeping the pressure at about 10 mbar; all solids in the mixture disappeared and a clear solution was obtained (about 1 hour). The amount of water collected in the cold trap was consistent with that expected by the reaction of boric acid with Fomblin® Z-DOL PFPE to form the corresponding triester (about 9 grams).

The mixture was analyzed by $^{19}$F-NMR: besides the well known signals of the OC$\underline{F}_2$CH$_2$OH group at −81.3 and −83.3 ppm (ref. CFCl$_3$), new signals appeared at −80.6 and −82.6 ppm, corresponding to the borate ester —OC$\underline{F}_2$CH$_2$O—B≡ groups. The ratio between the alcohol groups linked to the boron and the free alcohol groups was 30:70, as expected by the quantitative conversion of boric acid into the corresponding triester with Fomblin® Z-DOL PFPE.

Preparation 2—Preparation of Mixture [M1] (Fomblin® Z-DOL PFPE Potassium Salt)

In a separate 5 L reactor, 3.50 kg of the same Fomblin® Z-DOL PFPE as used in preparation 1) were charged and added with 75.5 g of a 30% aqueous solution of KOH (404 mmoles). The stirred mixture was heated at 80° C. under vacuum (from 50 mbar down to 10 mbar) until complete elimination of water and obtainment of a clear solution containing Fomblin® Z-DOL PFPE potassium salt.

The solution was cooled down to room temperature and added under stirring with 1.5 kg of the boric ester from preparation 1), thereby obtaining a clear solution.

Preparation of Mixture [M3]

The solution from preparation 2 (5.0 kg) was charged into a 10 L reactor and 20 g dried potassium iodide was added. The resulting mixture was heated at 80° C. under stirring and stripped with a nitrogen flow to remove water traces. The temperature was raised to 110° C. and the reactor evacuated.

Ethoxylation Reaction (Preparation of Mixture [M4])

Ethylene oxide (EO) was fed in the reactor up to a pressure of 3.5 atm and consumption of EO was readily observed by the pressure decrease. EO was continuously fed in order to maintain the pressure between 3 and 3.5 atm.

After 1.5 hours about 380 g EO were fed and soon afterwards the consumption rate started to slow down. The temperature was then gradually increased up to 140° C. in a time range of 2.5 hours; at this temperature a fast EO consumption was observed and in about 1.5 hours additional 740 g of EO were fed. EO feeding was stopped and within 45 minutes the pressure inside the reactor decreased from 3.5 atm down to 1 atm. The reaction mixture was cooled, stripped with nitrogen to eliminate dissolved residual EO and about 6,100 g product were recovered.

Purification and Analysis of the Ethoxylated PFPE Diol 100 g of product from preparation 3 was diluted with 50 ml 1,3-hexafluoroxylene (HFX), added with 50 ml of a 20% potassium carbonate aqueous solution and the resulting mixture was vigorously stirred at 50° C. for 1 hour. The lower organic layer was separated and poured into a separating funnel containing a mixture consisting of 50 ml water and 10 g isobutanol and vigorously shaken. After phase separation, the lower organic layer was collected and submitted to distillation in order to remove the solvents (HFX, isobutanol). The residue, consisting of 97 g of a clear pale yellow liquid, was submitted to NMR analyses.

$^1$H-NMR (solution in A113/CD$_3$OD) and $^{19}$F-NMR analyses confirmed the following structure:

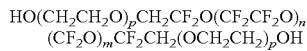

with an average ethoxylation degree p of 4.4 and content of non ethoxylated Fomblin® Z-DOL PFPE hydroxyl groups close to 0.3% (conversion exceeding 99%). $^{13}$C-NMR spectroscopy confirmed the ethoxylation degree value obtained by $^1$H-NMR. Inductively Coupled Plasma (ICP) analysis revealed a negligible content of boron (5 ppm).

Example 2

Sythesis of an Ethoxylated PFPE Diol with Average Ethoxylation Degree of 5

Preparation 1—Preparation of Mixture [M1]

6.40 kg Fomblin® Z-DOL PFPE as defined in Example 1 were charged in a 10 L reactor and added with 82.9 g of a 30% aqueous solution of KOH (440 mmoles KOH). The mixture was stirred and heated at 80° C. under vacuum (from 50 mbar down to 10 mbar) until complete elimination of water.

Preparation 2—Preparation of Mixture [M2]

The reactor was cooled to 60° C., then 25 g trimethylborate (240 mmoles) were added and the resulting mixture was stirred for half an hour under a slight nitrogen overpressure (0.2 bar), then vacuum was applied and the temperature was raised again to 80° C. until complete removal of methanol.

Preparation 3—Preparation of Mixture [M3]

Then 25 g of KI dispersed in slurry with 250 g of the starting dialcohol were added to the mixture and the reactor was stripped with a nitrogen flow for 15 minutes.

Ethoxylation Reaction (Preparation of Mixture [M4])

The temperature of mixture [M3] was raised to 110° C. and the reactor was evacuated. EO was fed up to a pressure of 3.4 atm (about 270 g) and consumption of EO was readily observed from pressure decrease. EO was continuously fed in order to maintain the pressure between 3 and 3.5 atm, using an automatic pressure control.

After 1.5 hours about 550 g EO were fed in the reactor, then consumption rate slowed down and after an additional hour no further feeding of EO was observed. Temperature was then increased to 140° C. in about half an hour and consumption of EO was again observed. The consumption rate became faster and faster and after about 2 hours and overall amount of 1.690 g EO (38.4 moles) had been fed to the reactor. Feeding was stopped and within 45 minutes the pressure inside the reactor decreased from 3.5 atm to 1 atm. The reaction mixture was cooled, stripped with nitrogen to remove dissolved residual EO and about 8,300 g of product were discharged from the reactor.

Purification and Analysis of the Ethoxylated PFPE Diol

An aliquot of this material was purified and analysed following the same procedure as in Example 1.

The $^1$H-NMR (solution in A113/CD$_3$OD) and $^{19}$F-NMR analyses confirmed the following structure:

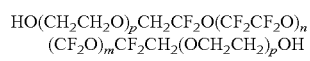

with average ethoxylation degree p=5.0 and content of non ethoxylated Fomblin® Z-DOL PFPE hydroxyl groups close to 1.0% (conversion 99%).

Example 3

Sythesis of an Ethoxylated PFPE Diol with Average Ethoxylation Degree of 4.5

Preparation 1—Preparation of Mixture [Mest]

Following the same procedure as in Example 1, 5.0 kg of Fomblin® Z-DOL PFPE having Mn=1,530 and Ew=845 were reacted with 18.3 g of boric acid (296 mmoles) to provide a solution of the corresponding triester of boric acid with Fomblin® Z-DOL PFPE in Fomblin® Z-DOL PFPE.

Preparation 2—Preparation of mixture [M1]

In a separate reactor, 2,500 g of the same Fomblin® Z-DOL PFPE were treated with 55.2 g of a 30% solution of KOH (296 mmoles of KOH) to provide a solution of the corresponding Fomblin® Z-DOL PFPE potassium alkoxyde in Fomblin® Z-DOL PFPE.

Preparation 3—Preparation of Mixture [M2]

[M$_{est}$] and [M1] were combined to provide 7.5 kg of a mixture [M2] containing the triester of Fomblin® Z-DOL PFPE with boric acid and Fomblin® Z-DOL PFPE potassium alkoxide in a 1:1 ratio.

Preparation of Mixture [M3]

Mixture [M2] from Preparation 3 was then charged into a 10 L and 35 g of dried potassium iodide were added. The mixture was heated to 80° C. under stirring and stripped with a nitrogen flow to remove traces of water, then the temperature was raised to 110° C. and the reactor was evacuated.

Ethoxylation Reaction (Preparation of Mixture [M4])

EO was fed in the reactor up to a pressure of 3.5 atm; after 2 hours no pressure reduction was observed. The temperature was gradually increased to 125° C. and at this temperature a very slow decrease of pressure was observed, but after 4 hours only about 100 g of EO were consumed. The reactor was left at 125° C. overnight, without feeding EO. The next morning the pressure was below 1 atm. About 450 g of EO were fed in order to restore the pressure at 3.5 atm. A slow pressure decrease was observed during time, similar to the one observed the day before. After 1 hour the temperature was increased to 140° C. 1.5 h; later on, EO consumption rate become progressively faster and in the next 2 hours additional 960 g of EO were fed. EO feeding was stopped and within 1 hour the pressure inside the reactor decreased from 3.5 atm to 1 atm. The reaction mixture was cooled, stripped with nitrogen to remove residual dissolved EO and about 9.0 kg of product were recovered from the reactor.

Purification and Analysis of the Ethoxylated PFPE Diol

An aliquot of the product was purified and analysed following the procedure of Example 1.

$^1$H-NMR (solution in A113/CD$_3$OD) and $^{19}$F-NMR analyses confirmed the following structure:

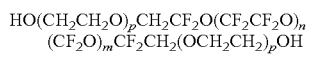

HO(CH$_2$CH$_2$O)$_p$CH$_2$CF$_2$O(CF$_2$CF$_2$O)$_n$
(CF$_2$O)$_m$CF$_2$CH$_2$(OCH$_2$CH$_2$)$_p$OH with an average ethoxylation degree p=4.5 and content of non ethoxylated Fomblin® Z-DOL PFPE hydroxyl groups close to 4.4% (conversion 95%). $^{13}$C-NMR spectroscopy confirmed the ethoxylation degree value obtained by $^1$H-NMR and Inductively Coupled Plasma (ICP) analysis revealed a negligible content of boron (9 ppm).

Example 4 (Comparative Example)

Ethoxylation of Fomblin® Z-DOL PFPE with a Defect of Fomblin® Z-DOL PFPE Alkoxide Following the same procedure as in Example 1, 2.0 kg of Fomblin® Z-DOL PFPE Mn=1,410 and Ew=777 were reacted with 20.0 g of boric acid (320 mmoles) to obtain a solution of the corresponding borate triester in Fomblin® Z-DOL PFPE.

In a separate reactor, 1500 g of the same of Fomblin® Z-DOL PFPE were treated with 48.5 g of a 30% solution of KOH (260 mmoles of KOH) to obtain a solution of the corresponding alkoxide in Fomblin® Z-DOL PFPE. The two solutions were mixed to provide 3.5 kg of a solution containing the borate triester and a defect of alkoxide (with respect to triester) in Fomblin® Z-DOL PFPE.

This solution was charged into a 10 L ethoxylation reactor and 15 g of dried potassium iodide were added. The mixture was heated at 80° C. under stirring and stripped with a nitrogen flow to eliminate traces of water.

Temperature was raised to 110° C. and the reactor evacuated. EO was fed in the reactor up to a pressure of 3.5 atm. After 2 hours no pressure reduction was observed. The temperature was gradually increased to 140° C., but no reaction was observed. After one hour, the temperature was further increased to 150° C. (part of the EO was vented in order to maintain the pressure below 6 atm) but again no pressure reduction was observed. Using the same procedure, the temperature was increased up to 160° C. and then to 175° C., but no pressure reduction was observed after 2 hours, so the experiment was stopped.

This example thus demonstrate that, if ethoxylation is carried out using a defective amount of PFPE alkoxide with respect to the PFPE boric acid triester, the ethoxylation reaction does not proceed.

Example 5 (Comparative Example)

Ethoxylation of Fomblin® Z-DOL PFPE with No Fomblin® Z-DOL PFPE Alkoxide

Following the same procedure as in Example 1, 5,100 g of a ZDOL having Mn=1,530 and Ew=845 were reacted with 37.1 g of boric acid (600 mmoles) to obtain a solution of the corresponding borate triester in Fomblin® Z-DOL PFPE.

This solution was then charged into a 10 L ethoxylation reactor and 20 g of dried potassium iodide were added. The mixture was heated at 80° C. under stirring and stripped with a nitrogen flow to remove traces of water. The temperature was raised to 110° C. and the reactor was evacuated. EO was fed into the reactor up to a pressure of 3.5 atm; no pressure reduction was observed. The temperature was gradually increased to 140° C., but no reaction was observed. After one hour the temperature was further increased to 150° C. (part of the EO was vented in order to maintain pressure below 6 atm) but again no pressure reduction was observed. Following the same procedure, the temperature was increased up to 160° C., then to 170° C. and finally to 180° C., but no reaction was observed even at the highest temperature, so the experiment was stopped.

The trial was repeated exactly under the same conditions, except that 250 g of the polyethoxylated PFPE obtained in Example 1 (with ethoxylation degree p=4.4) were added to the initial reaction mixture. The same ethoxylation procedure as above was used, but no reaction was observed up to 180° C., so the experiment was stopped.

This example thus demonstrates that, if ethoxylation is carried out without a catalytic amount of PFPE alkoxide, ethoxylation does not occur.

The invention claimed is:

1. A process for preparing an alkoxylated derivative of a (per)fluoropolyether (PFPE) alcohol, the process comprising:
   1) separately providing a mixture [M1], comprising a PFPE alcohol and a catalytic amount of the corresponding alkoxide;
   2) bringing into contact mixture [M1] with a boric acid triester of the same PFPE alcohol in an amount such that the molar ratio between the PFPE alkoxide and the boric acid triester is at least 1, to obtain a mixture [M2];
   3) contacting mixture [M2] with a catalytic amount of an iodine source to obtain a mixture [M3];
   4) treating mixture [M3] with an alkoxylating agent to provide a mixture [M4] containing an alkoxylated derivative of the PFPE alcohol.

2. The process according to claim 1 wherein the PFPE alcohol comprises a partially or fully fluorinated, straight or branched, polyoxyalkylene chain (chain R$_f$) having at least two chain ends, wherein one or both chain end(s) bear(s) at least one hydroxyl group.

3. The process according to claim 2, wherein the PFPE alcohol comprises an R$_f$ chain having two chain ends, wherein one chain end bears one hydroxyl group.

4. The process according to claim 2, wherein the PFPE alcohol comprises an $R_f$ chain having two chain ends, wherein both chain ends each bear one hydroxyl group.

5. The process according to claim 1, wherein the PFPE alcohol complies with formula I:

$$A-O-R_f-(CF_2)_x-CFZ-CH_2OH \quad (I)$$

wherein:
R$_f$ is a (per)fluoropolyoxyalkylene chain having an average number molecular weight $M_n$ ranging from 100 to 8,000 and comprising repeating units, which may be equal to or different from one another, selected from the following groups: (CFYO), wherein Y is F or $CF_3$; $(CF_2CF_2O)$; $(C_3F_6O)$; and $(CF_2CF_2CF_2O)$ Z is fluorine or $CF_3$;

x is 0 or 1, with the proviso that, when x is 1, Z is F;

A is $-(CF_2)_x-CFZ-CH_2OH$ or is selected from straight or branched $C_1$-$C_4$ perfluoroalkyl groups wherein one fluorine atom can be optionally substituted by one chlorine atom or one hydrogen atom; provided that, when chlorine is present in group A, it is in a molar amount lower than 2% with respect to the overall amount of end groups.

6. The process of claim 5, wherein chain $R_f$ is selected from the following classes:

$$-(CF_2O)_n(CF_2CF_2O)_m(CF_2CF_2CF_2O)_p(CF_2CF_2CF_2CF_2O)_q- \quad (a)$$

wherein m, n, p, q are 0 or integers selected such that chain $R_f$ has an average number molecular weight $M_n$ ranging from 100 to 8,000;

$$-(CF_2CF(CF_3)O)_a(CF_2CF_2O)_b(CF_2O)_c(CF(CF_3)O)_d- \quad (b)$$

wherein a, b, c, d are 0 or integers selected such that chain $R_f$ has an average number molecular weight $M_n$ ranging from 100 to 8,000;

$$-(CF_2CF(CF_3)O)_e(CF_2O)_f(CF(CF_3)O)_g- \quad (c)$$

wherein e, f, g are 0 or integers selected such that chain $R_f$ has an average number molecular weight $M_n$ ranging from 100 to 8,000.

7. The process according to claim 1, wherein the molar ratio between the PFPE alkoxide and the boric acid triester is greater than 1.

8. The process according to claim 7, wherein the molar ratio between the PFPE alkoxide and the boric acid triester is least 2.

9. The process according to claim 1, wherein the triester of the PFPE alcohol with boric acid is prepared separately from mixture [M1] and then brought into contact with mixture [M1].

10. The process according to claim 1, wherein the triester of the PFPE alcohol with boric acid is prepared in situ by adding to [M1] a boric acid alkyl ester.

11. The process according to claim 1, wherein the iodine source is iodine.

12. The process according to claim 1, wherein the alkoxylating agent is ethylene oxide or propylene oxide.

13. The process according to claim 1 wherein the alkoxylating agent is ethylene oxide.

14. The process according to claim 1, wherein the alkoxylated alcohol has an alkoxylation degree of at least 2.

15. The process according to claim 14 wherein the alkoxylation degree ranges from 2 to 10.

16. The process according to claim 6, wherein chain $R_f$ is $-(CF_2O)_n(CF_2CF_2O)_m-(CF_2CF_2CF_2O)_p(CF_2CF_2CF_2CF_2O)_q-$ and wherein the ratio of m/n is between 0.1 and 20, extremes included, when m is other than 0 and the ratio of (p+q)/(m+n) is between 0 and 0.2, extremes included, when (m+n) is other than 0.

17. The process according to claim 6, wherein chain $R_f$ is $-(CF_2CF(CF_3)O)_a(CF_2CF_2O)_b(CF_2O)_c(CF(CF_3)O)_d-$ and wherein the ratio of a/b is between 0.1 and 10 when b is other than 0 and the ratio of (c+d)/(a+b) is between 0.01 and 0.5 when (a+b) is other than 0.

18. The process according to claim 6, wherein chain $R_f$ is $-(CF_2CF(CF_3)O)_e-(CF_2O)_f(CF(CF_3)O)_g-$ and wherein the ratio of (f+g)/e is between 0.01 and 0.5 when e is other than 0.

* * * * *